United States Statutory Invention Registration [19]

[11] Reg. Number: H831

Salanitro et al. [43] Published: Oct. 2, 1990

[54] TUBULAR BIOFILM REACTOR

[75] Inventors: Joseph P. Salanitro; James S. Hokanson, both of Houston, Tex.

[73] Assignee: Shell Oil Company, Houston, Tex.

[21] Appl. No.: 39,851

[22] Filed: Apr. 20, 1987

Related U.S. Application Data

[63] Continuation of Ser. No. 603,016, Apr. 23, 1984, abandoned.

[51] Int. Cl.[5] ..... C12Q 1/04; C12Q 1/24; C12M 1/32; C12M 1/28

[52] U.S. Cl. ..... 435/34; 435/30; 435/293; 435/294

[58] Field of Search ..... 435/30, 31, 34, 287, 435/292, 293, 294, 813, 819; 73/863.71, 863.85

[56] References Cited

U.S. PATENT DOCUMENTS

| | | | |
|---|---|---|---|
| 1,510,195 | 9/1924 | Romer | 435/819 X |
| 1,837,858 | 12/1931 | Grace | 73/863.71 |
| 2,484,279 | 10/1949 | Folz | 73/863.85 X |
| 3,083,577 | 4/1963 | Nelson et al. | 73/863.71 |
| 3,591,454 | 7/1971 | Laatsch | 435/819 X |

OTHER PUBLICATIONS

Brochure from Microbios Ltd., Calgary, Alberta, Canada, re "The Robbins Biofilm Sampler".

"Biocide Testing Against Corrosion-Causing Oil-Field Bacteria Helps Control Plugging", article from Oil & Gas Journal, Mar. 8, 1982, pp. 253-264.

"Observations of Fouling Biofilm Formation", W. F. McCoy, et al, 1981 National Research Council of Canada, pp. 910-917.

*Primary Examiner*—John F. Terapane
*Assistant Examiner*—John M. Covert

[57] ABSTRACT

A tubular connected series of biofilm samplers is provided for monitoring biofouling by microorganisms in a continuous flow stream. Tubular bypasses are provided around each sampler, so that each sampler is removable for inspection of biofouling without interruption of the continuous flow stream. In addition, each sampler has a contoured surface which is in contact with the continuous flow stream and which is flush with the inner surface of the tubulars connecting the samplers.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TUBULAR BIOFILM REACTOR

This is a continuation of application Ser. No. 603,016, filed Apr. 23, 1984, now abandoned.

BACKGROUND OF THE INVENTION

Commercial biocides are used to control the growth of microorganisms in flowing or stagnant systems (piping, transit lines, tanks, cooling water and waste water systems) which can become fouled due to biofilm development. In many flowing aquatic systems, bacteria are able to adhere to a variety of surfaces (steel, glass, plastic). Bacterial attachment to surfaces is affected by several factors including surface charge and energy, hydrophobicity, nutrient availability, fluid flow and shear, microorganism type and temperature. As colonization progresses, microbes absorb nutrients from the flowing fluid, grow as an adhered biomass and produce extracellular slime. The fibrillar network of slime allows the cells to attach to each other and maintain successive populations on the adhering surface. The fouling biomass can eventually increase frictional resistance of fluid flow and in severe cases cause plugging of a tubular system. In addition, biofouled surfaces of metals undergo a progressive deterioration characterized by complex chemical and biochemical oxidation-reduction reactions in which bacteria (e.g. sulfate-reducing bacteria) can initiate or accelerate the corrosion process.

In studies of biofilm formation, McCoy et al (1981, Canad, J. Microbial. 27:910) and Ruseskca et al (1982, Oil and Gas J., March 8, pp 253–264) have described a continuous flow tubular recycle reactor for biofilm sampling (hereinafter referred to as the Robbins device) which can be placed as a bypass or slipstream into an existing flow system. The Robbins device has removable test surfaces (studs) for studying the development of biofilm growth and evaluating biocide effectiveness. The present invention is an improvement over the Robbins device, which suffers from several inadequacies, as will be described more particularly hereinafter.

SUMMARY OF THE INVENTION

The primary purpose of the present invention is to provide a method and apparatus for monitoring biofouling by microorganisms in a continuous flow stream, which produce accurate results and which do not interfere with the continuous flow stream being monitored. Accordingly, an apparatus is provided for monitoring biofouling by microorganisms in a continuous flow stream, wherein tubulars connect a series of biofilm samplers and provide bypasses around each sampler, and whereby each sampler is removable for inspection without interruption of the continuous flow stream. Preferably, each sampler has a contoured surface which is in contact with the continuous flow stream and flush with the inner surface of the tubular means.

The present invention also pertains to a method for monitoring biofouling by microorganisms in a continuous flow stream, including connecting a series of biofilm samplers with tubulars, bypassing the continuous flow stream around at least one of the biofilm samplers, and checking the bypassed biofilm sampler for biofouling. Preferably, the method includes positioning each sampler such that a contoured surface of the sampler is in contact with the continuous flow stream and flush with the inner surface of the tubular means.

Other purposes, distinctions over the art, advantages and features of the invention will be apparent to one skilled in the art upon review of the following.

DESCRIPTION OF PREFERRED EMBODIMENTS

Traditional biocide testing, e.g., in cell suspension (free-floating or planktonic organisms) assays, has been inadequate for inhibiting aerobic and anaerobic organisms that colonize surfaces (sessile or adherent populations). Higher doses of an antimicrobial agent which are active against the free-floaters at lower levels, are required to kill or reduce the sessile organisms accumulating on surfaces. Attached microbes are more refractory to biocide inhibition mainly because these compounds cannot penetrate the biofilm surface with its many layers of cells and exocellular polysaccharide slime.

In oilfield waterflood operations water-borne aerobic organisms and sulfate-reducing bacteria can potentially cause biofouling and corrosion of injection and production tubulars, water treating facilities and transfer lines. It is possible through the prudent field use of biocides to control adherent microbial growth, a substantial savings in yearly replacement cost of corroded and biofouled piping can be obtained. This need in the art has led to the present invention which is a continuous flow tubular device which can be used to screen biocides for biofilm control. The present invention differs from the above-discussed Robbins device in that it (a) is constructed of stainless steel and can be used with saline water (e.g. seawater), (b) can be operated under high pressure (up to about 1500 psi, or greater), and therefore, simulate injection pressures of tubulars entering well-bore zones in a reservoir, (c) can be operated at high flow (up to about 1.5 liters per minute, or greater, through the tubular) of field injection systems, and (d) has a system of shut-off valves for continuous biofilm sampling without interfering with flow through the pressurized tubular.

The following describes the construction and operation of the present invention which can (1) detect adherent populations of sulfate-reducing bacteria, and aerobic organisms or the like in a flowing tubular system, and (2) be used to determine optimum biocide levels and dosing regimes to control such biofouling.

Figure 1:
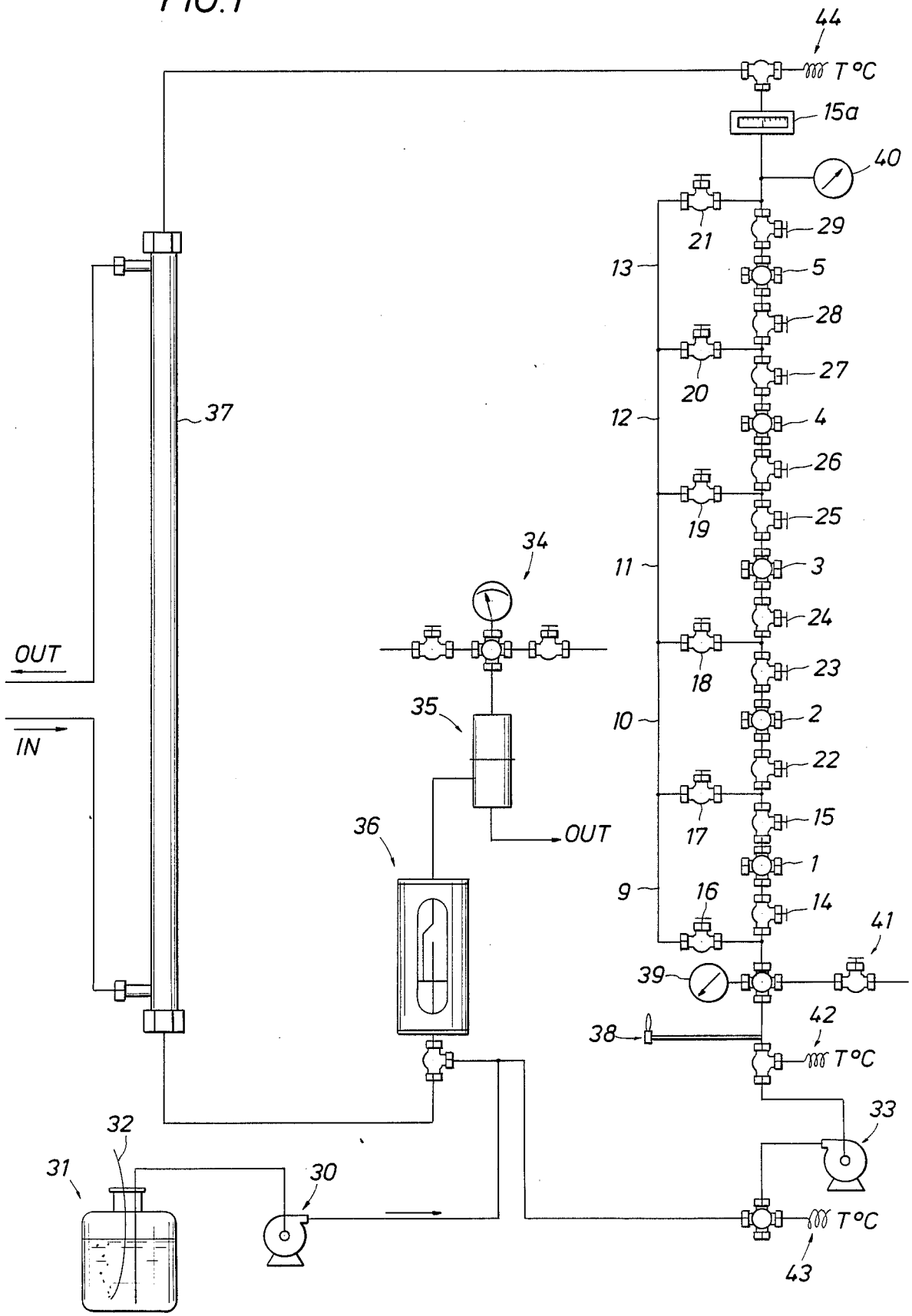
FIG. 1 is a schematic of a high pressure/high flow rate tubular biofilm reactor.
Figure 2:
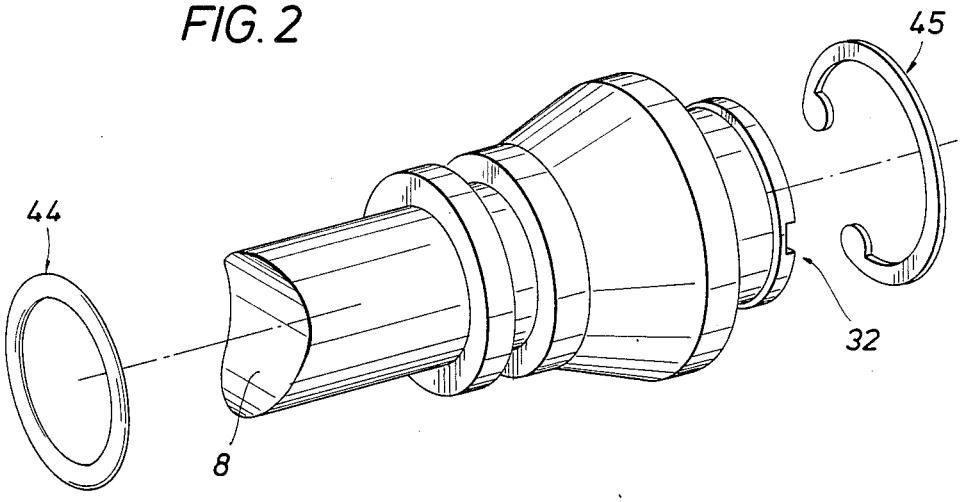
FIG. 2 shows a biofilm sampler.
Figure 3:
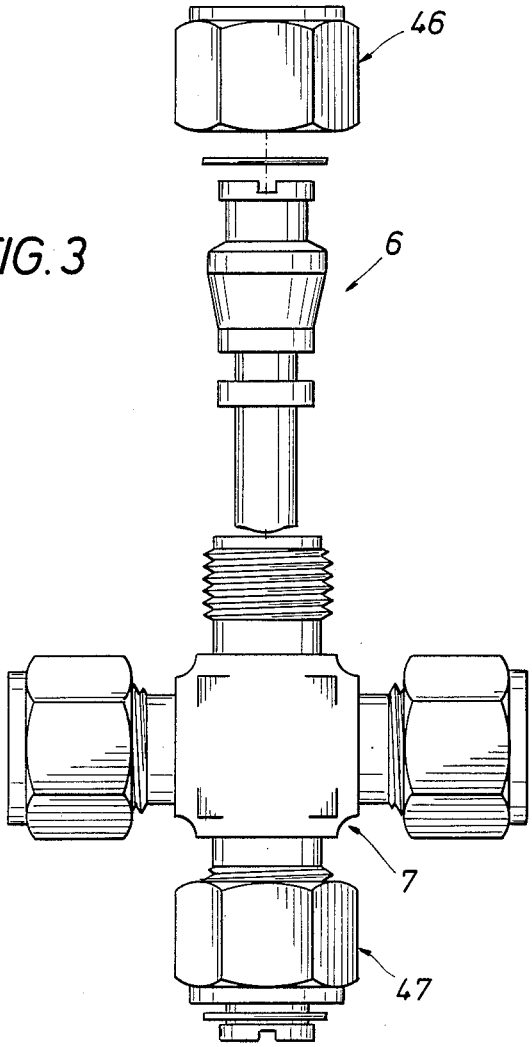
FIG. 3 shows a holder for the biofilm sampler.
Figure 4:
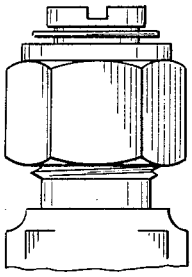
FIG. 4 shows a biofilm sampler, such as shown in FIG. 2, inserted into the holder, such as shown in FIG. 3.

Schematics for the continuous flow tubular system and the biosamplers of the invention are shown in FIGS. 1–3. The entire tubular system, preferably about ¼-inch inside diameter tubing, and all valves and all four-way fittings are preferably made of stainless steel and have a maximum pressure rating of approximately 5000 psi or greater. Each four-way fitting 1–5 contains two studs or biosamplers, such as samplers 6 and 7 shown in FIG. 3 which are machined to set flush with the inside of the tubular wall. Biofilm growth occurs on the flush-fitting concave surface 8 shown in FIG. 2. The biosamplers are preferably manufactured of carbonless steel or stainless steel. The process of the invention requires connecting at least two biofilm samplers with tubular means. The tubular system is equipped with bypasses 9–13 around each pair of biosamplers in each four-way fitting 1–5, for diverting fluid flow. This allows for inspecting the biosamplers while the tubular system is operating continuously under high pressure and flow. To bypass four-way fitting 1, for example, valves 14 and 15 are closed, and valves 16 and 17 are opened (while valves 18–21 remain closed and valves 22–29 remain open). Other combinations of open and closed valves can be utilized to bypass any one, combination or all of the four-way fittings. For example, valves 14 and 29 may be closed and valves 16 and 21 opened (while valves 17–20 remain closed) in order to bypass all the four-way fittings.

Pump 30 supplies fluid for analysis from container 31 which may contain, for example, seawater. A flush line 32 is provided to pressure the container, for example with nitrogen. A recirculating fluid pump 33 is utilized to provide circulation through the four-way fittings 1–5. Both pumps preferably are rated at pressures of at least about 1500 psi. Pressure in the tubular system is supplied from back pressure regulator 34, preferably using deoxygenated nitrogen and a high capacity gas purifier 35 with a bottoms drawoff, e.g. $H_2O$-$N_2$. The tubular reactor is also equipped with a Jorgenson gauge 36 for removing any excess entrained gases. A coaxial heat exchanger 37 is used for removing heat generated during the temperature control experiments (with heating fluid, e.g. $H_2O$, shown going in and out), and a pulsation dampener 38 is used to reduce large pulse variations from the recirculating pump 33. Pressure relief valves 39 and 40 are provided as safety measures for potential pressure increases in the system, along with over pressure relief 41. In addition, temperature checks 42–44 are used to monitor temperature changes, and a rotameter **15*a*** is provided to check flow rates.

FIGS. 2 and 3 provide an exploded view of the biofilm sampler and holder. The biofilm sampler utilizes an O-ring 44 and a locking ring 45 to hold the sampler in place with lock nuts 46 and 47 in the holder shown in FIG. 3. Preferably, when the sampler is secured in place in the four-way fitting, as shown on the right hand side of FIG. 2, the groove is aligned to properly orient the surface 8 with respect to the inside walls of the tubulars.

The foregoing description of the invention is merely intended to be explanatory thereof, and various changes in the details of the described method and apparatus may be made within the scope of the appended claims without departing from the spirit of the invention.

What is claimed is:

1. A method for monitoring biofilm mieroorganisms in a continuous flow stream, comprising (a) connecting biofilm samplers with tubular means, (b) passing a continuous flow stream through the samplers, (c) bypassing the continuous flow stream around at least one biofilm sampler, and (d) checking the one biofilm sampler for biofouling.

* * * * *